United States Patent [19]

Greenfield

[11] Patent Number: 4,804,267

[45] Date of Patent: Feb. 14, 1989

[54] SYSTEM FOR MICROSCOPICALLY ANALYZING FLUIDS

[75] Inventor: Walter Greenfield, Scarsdale, N.Y.

[73] Assignee: Scientific Imaging Instruments, Inc., Fairfield, Conn.

[21] Appl. No.: 883,365

[22] Filed: Jul. 10, 1986

[51] Int. Cl.[4] .................... G01N 21/05; G01N 21/84
[52] U.S. Cl. .................... 356/335; 356/246; 356/410; 356/440; 358/93
[58] Field of Search .............. 250/573, 576; 356/244, 356/246, 409, 410, 440, 335; 358/93

[56] References Cited

U.S. PATENT DOCUMENTS

| | | | |
|---|---|---|---|
| 2,954,472 | 9/1960 | Frenzel | 356/246 |
| 3,552,865 | 1/1971 | Leung et al. | 356/246 |
| 4,367,043 | 1/1983 | Sweet et al. | 356/244 |
| 4,393,466 | 7/1983 | Deindoerfer et al. | 356/335 |
| 4,486,097 | 12/1984 | Riley | 356/410 |
| 4,612,614 | 9/1986 | Deindoerfer et al. | 356/335 |

Primary Examiner—F. L. Evans
Attorney, Agent, or Firm—Kenyon & Kenyon

[57] ABSTRACT

An apparatus for microscopically analyzing fluids consisting of subsystems for providing fluid flow and for acquiring and displaying an image. The fluid flow subsystem pumps a portion of the fluid sample from a sample container to a flow-through cell, where a thin planar portion of sample is presented for viewing. The flow-through cell includes a three-part lamination, the two outer members being generally flat and the center member having a display chamber cut out of its central portion. The fluid flow subsystem also includes means for washing the subsystem between samples, by pumping a quantity of solvent through the flow-through cell, the pump and associated tubing. A light beam is passed through the flow-through cell, enabling a video camera to acquire a magnified image of a portion of the sample, which image is displayed on a monitor.

4 Claims, 3 Drawing Sheets

SYSTEM FOR MICROSCOPICALLY ANALYZING FLUIDS

BACKGROUND OF THE INVENTION

This invention relates to the field of medical instrumentation, and more specifically to the field of microscopic analysis of fluids.

Suppliers of medical instrumentation have adopted computer technology to a high degree, offering complex and expensive equipment capable of providing rapid analyses and calculations. Such equipment has proved its worth in many situations, and indeed has paved the way to more exact, efficient diagnosis. Computerized axial tomography, for example, literally has revolutionized diagnositic techniques.

This trend, however, has bypassed some of the more mundane but essential tasks faced by the medical laboratory. Urinalysis presents an excellent example of this phenomenon. The task is relatively straightforward: a technician must view a sample through a microscope and count the number of white blood cells in a given area. Following traditional methods, the technician places a drop of sample on a microscope slide, covers that slide with a cover slide, and clips the assembly on the viewing stage of a microscope. After making the count, the two-slide assembly usually is discarded.

The answer offered by equipment suppliers is complete automation of urinalysis, combining computer-controlled chemical testing with optical scanning and pattern recognition to generate a complete report in a matter of seconds. In an era when rising medical costs are a matter of national concern, however, new equipment must not only be technically sophisticated but also cost effective. Many laboratories have rejected the automated approach after carefully weighing the savings provided versus the costs associated with the high level of capital expenditure required.

Yet, laboratories recognize that tasks such as urinalysis are expensive, labor-intensive, and repetitive. A 300-bed hospital, for example, will perform almost 23,000 urinalyses per year; at a cost of about $0.25 in disposables for each analysis, this testing results in an expenditure of almost $5700, plus the cost of technicians and microscopes, etc. This level of spending certainly does not justify the purchase of equipment priced over $100,000, but the clear requirement exists to reduce costs. What laboratories need is an approach that offers the benefits of automation without travelling as far as the fully computerized systems provided by the instrumentation industry.

The art has failed to provide effective solutions to this problem. U.S. Pat. Nos. 3,864,564, to Adkins, and 3,397,656 disclose automated systems for positioning and viewing samples, employing sophisticated logic circuitry and complex mechanisms for driving the slide in selected patterns to insure full scanning. Such approaches typify the problem rather than the solution. Similarly, Negersmith, in U.S. Pat. No. 4,300,906 presents an improvement to an automated analysis system designed to provide a constant flow of sample through the analytical portion of the system. Again, such systems do not meet the needs of the laboratories for a urinalysis system.

An optical counting system is disclosed in U.S. Pat. No. 3,511,573, issued to Isreeli, stated as being particularly useful for counting red blood cells. There, a flow cell is employed in conjunction with means for focusing a light beam, the particles being detected by utilizing photocells and photomultipliers to sense occlusions of the beam. The flow cell of this invention is itself somewhat of a complex device, requiring the machining of bores and passageways and the inclusion of a special fitting to accomodate the washing function. In like manner, a flow cell is also disclosed in U.S. Pat. No. 3,515,491, to Emary, in which the sample is retained in a machined block, within a cylindrical insert having fluid passages and a viewing bore.

What none of these devices provide is an inexpensive, easy-to-use system that will allow a laboratory to automate its urinalysis without high capital expenditure. It was left to the inventor of the present invention to solve this problem.

SUMMARY OF THE INVENTION

An object of the present invention is to provide apparatus for microscopically analyzing fluids.

A further object of the invention is to provide apparatus that will enable urinalysis to be performed rapidly and conveniently.

Yet another object of the invention is a urinalysis system that allows a technician to perform urinalysis rapidly, eliminating danger of spillage and the eyestrain associated with conventional microscope equipment.

These and other objects are achieved by the present invention. In one embodiment of the invention, a urinalysis system is provided, consisting of subsystems for providing fluid flow and for acquiring and displaying an image. The fluid flow subsystem pumps a portion of fluid sample from a sample container to a flow-through cell, where a thin planar portion of sample is presented for viewing. The flow-through cell includes a three-part lamination, the two outer members being generally flat and the center member having a display chamber cut out of its central area. The fluid system also includes means for washing the system between samples, by pumping a quantity of solvent (pure water in the instance of a urinalysis system) through the flow-through cell, the pump, and associated tubing. A light beam is passed through the flowthrough cell, enabling a video camera to acquire a magnified image of a portion of the sample, which image is displayed on a monitor.

DETAILED DESCRIPTION OF A PREFERRED EMBODIMENT

Figure 1:
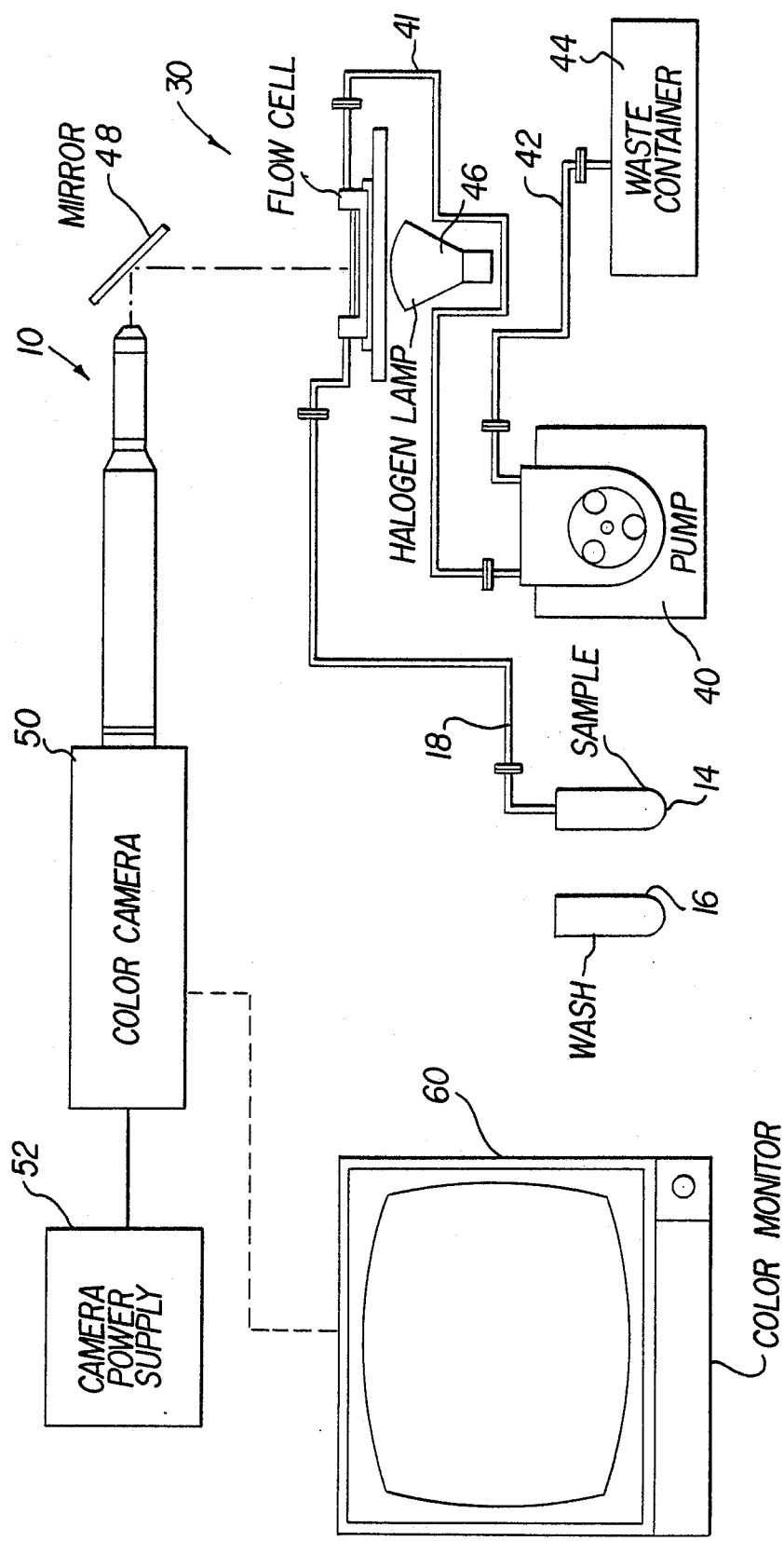
FIG. 1 is a schematic diagram of an embodiment of the invention.
Figure 2:
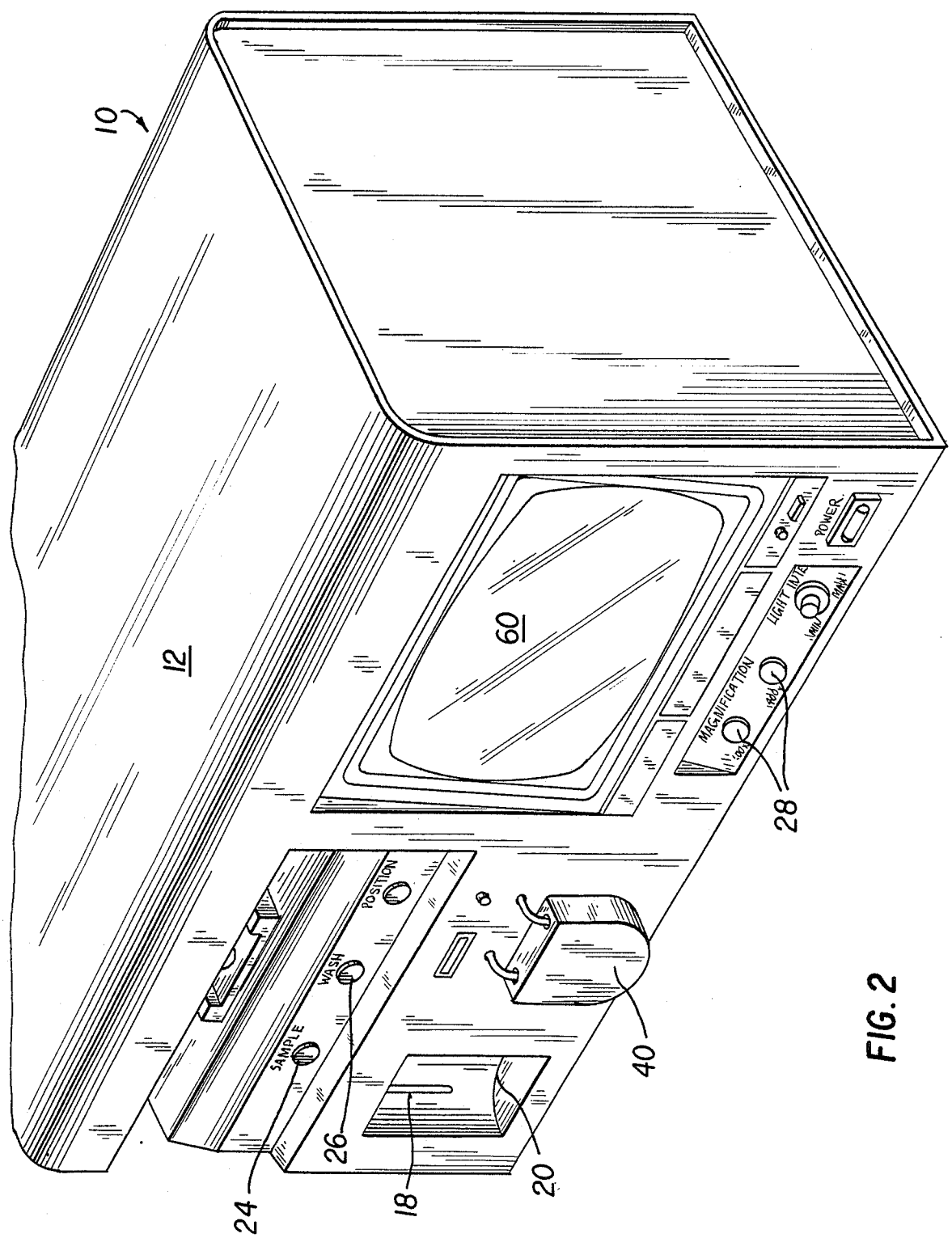
FIG. 2 is a pictorial showing the embodiment of FIG. 1 mounted in a housing.

FIG. 1 schematically depicts an embodiment 10 of the invention. Preferably, the system is contained within a unitary housing 12, as shown in FIG. 2, with accessible control and display features as described below.

The invention generally can be thought of as two cooperating subsystems—a fluid handling system and an imaging system. The former subsystem includes the components required to bring a portion of the sample into position for viewing, to dispose of the sample after analysis, and to purge the system between samples. The imaging subsystem consists of those elements needed to generate a magnified image of the sample and to display that image for analysis.

The fluid subsystem begins at one of two fluid sources—the sample container 14 or the wash reservoir 16. The latter can be a small tank, fabricated of a convenient inert plastic or other suitable material, carried within the housing. For urinalysis applications, distilled water serves as an excellent washing medium, and the reservoir preferably is connected to a water supply. Other analytical tasks might require different solvents, and those in the art will appreciate the best manner of selecting a particular solvent for individual requirements.

As urine specimens usually are provided to the laboratory in small containers, a sample well 20, sized to accept such containers, is formed in the front panel of the housing. A portion of the tubing 18 extends downward into the well, so that a sample container may be placed into the well with the tubing extending into the container. It should be noticed that the technician is not required to pour or remove any of the sample from the container, an advantage of the present invention. This convenient method not only results in a time savings, but also it prevents contamination of the work area resulting from spillage.

Only one of the two sources is connected to the remainder of the system at any given time. A two-way valve 22, selected from among the many suitable components available to the art, is actuated by front panel buttons 24 and 26 to select the appropriate alignment. From the two sources, the tubing 18 esxtends to the input end of the flow-through cell 30, discussed in greater detail below. Further tubing runs from the output end of the flow-through cell to a pump 40, which provides fluid pressure to the system. This pump should be capable of rapidly transporting a quantity of sample from its container to the flow-through cell, and it is preferred to employ a small peristalic pump, selected from among those commercially available in this role. For ease of service, the pump may be mounted on the front panel, as shown in FIG. 2. The pump output line 42 carries fluid to a waste container 44, which may further communicate with a drain line (not shown). Alternatively, the output line can feed directly to a drain if desired.

The imaging system consists of those elements required to produce a magnified image for analysis. As with conventional microscopes, a source of light is needed, and here that light is provided by lamp 46, which may be halogen or other suitable source of illumination known to those in the art. The beam emitted by this lamp passes through the portion of the specimen disposed in the flow-through cell and continues to camera 50. Size considerations of this embodiment dictated that the beam be reflected 90 degrees using mirror 48, but other in other applications the user may find that the beam can be passed to the camera in a straight line. Either method can be used.

Camera 50 can be a television camera, known to the art, fitted with a lens capable of providing magnification. It is preferred to offer two degrees of magnification, at 200 and 400 diameters, and the camera is selected to provide an optical system consistent with that requirement. The camera lens system should be of the "zoom" adjustable type, and is controlled from the front panel by selector buttons 28. Signals from the camera are connected to monitor 60, mounted in the front panel, where they are electronically processed to produce an image. To obtain an image that most exactly replicates the view observed directly through a microscope, it is preferred to employ a color camera and monitor having good optical resolution.

Figure 3:
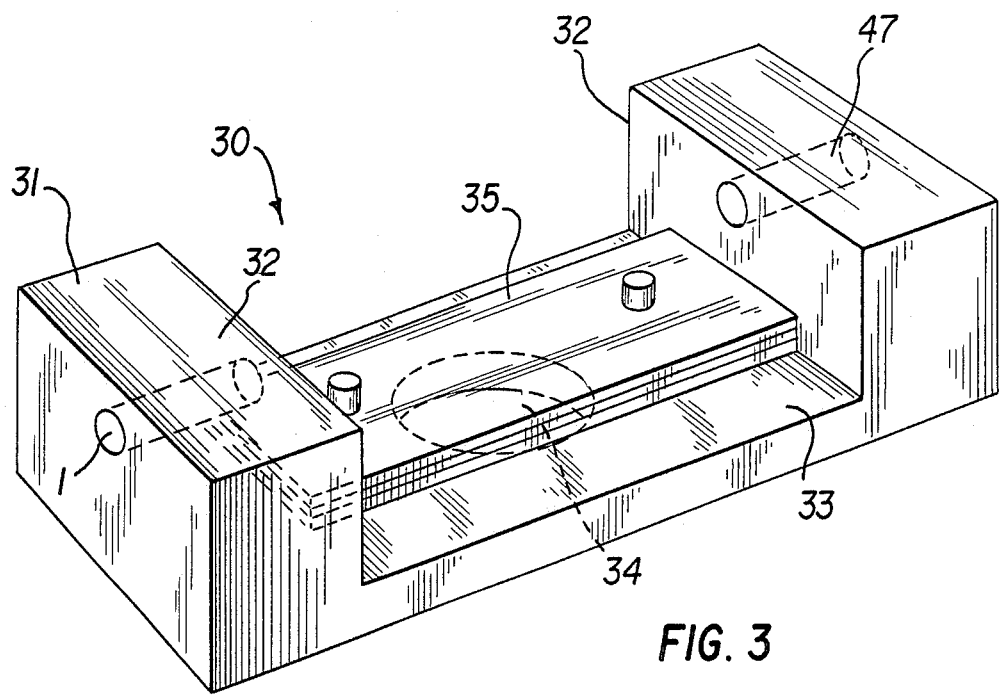
FIG. 3 is a pictorial of the flow-through cell of the embodiment shown in FIG. 1.

The intersection of the two subsystems is occupied by flow-through cell 30, better seen in FIG. 3. The cell body 32 is generally in the form of a flat letter "U", with upstanding end portions 31 and a central well 33. The body may be formed of any convenient material, but it has proved effective and economical to fabricate it from aluminum, which is readily available, light, and easy to work. A circular viewing aperture 34 lies at the center of the central well, extending completely through the body at that point. This opening may be sized according to the analysis task to be performed.

Figure 4:
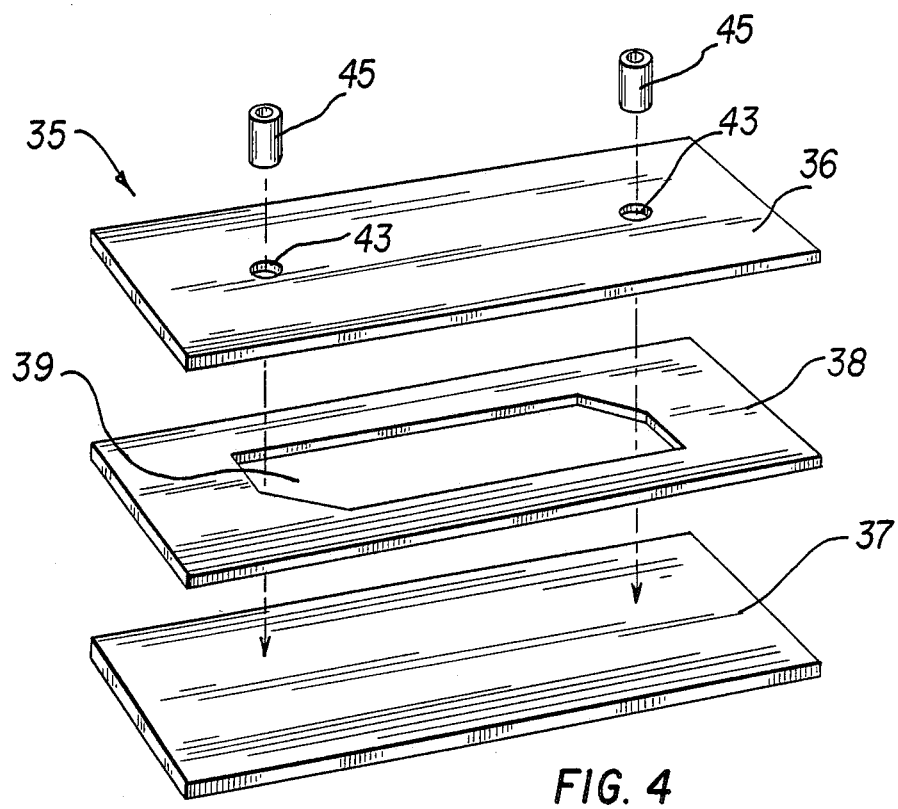
FIG. 4 is an exploded pictorial of the laminated display cell of the flow-through cell of FIG. 3.

A sample viewing assembly 35 is carried in the central well. This device accepts a portion of the sample and disposes it for optimum viewing by the camera. As shown in the exploded view of FIG. 4, this element is a lamination of three parts. Upper and lower retainers 36 and 37 are generally flat, transparent members that form the outer walls of the assembly. It has been found that these members can most conveniently be formed of glass slides commonly available, but of course those in the art will understand that other materials, such as any of a number of clear plastics, can be employed. The central element 38 has a cutout area in its central portion, display chamber 39. Utilizing a glass slide for this element insures that the sample will be presented to the imaging system in a thin planar form, allowing the technician to gain a clear view of the material within the sample.

Hollow connector pegs 45, secured in mounting holes 43 in upper retainer 36 and extending upward, allow for connection to fluid input and output tubing. It should be noted that the mounting holes are located at the extreme ends of the display chamber, to insure that fluid does flow throughout the chamber, with no portions of fluid being trapped behind an inlet or outlet port. The pegs are preferably fabricated of hollow metal tubing, and are secuered in the mounting holes with an appropriate cement. Cement also is applied to the retainers and to the center element to seal the display chamber and to maintain the assembly as a single unit. To prevent the application of sidewise stress to the connector pegs by the tubing, support passages 47 may be formed in the upstanding ends of the cell body, sized to accept the tubing.

Analysis of a sample proceeds straightforwardly. First, of course, the unit is turned on and the monitor adjusted, in a manner known to those in the art. A technician then places a sample container in the sample well 20 (FIG. 2), insuring that tubing 18 extends into the sample. When "Sample" button 24 is depressed, two-way valve 22 cycles to connect the fluid subsystem to the sample container 14, the pump 40 operates, drawing a portion of the sample into the flow-through cell 30. A portion of the sample enters the display chamber 39 as a relatively thin film of fluid. The beam of light emitted by lamp 46 passes through the sample, is reflected by mirror 48, and enters video camera 50, which generates a video image displayed on monitor 60. The technician can choose between two levels of magnification by appropriate selection of buttons 28.

When analysis is complete, the technician presses "Wash" button 26. Two-way valve 22 cycles to connect the fluid subsystem to the wash reservoir 16, and the pump operates to draw a quantity of pure water through the tubing, the flow-through cell and the pump, removing all traces of the previous sample. Both the excess sample and the wash water are pumped into the waste container. At this point the technician can perform another analysis by replacing the sample container with another such container and repeating the steps outlined above. It should be noted that after each analysis, the pump propels a sufficient quantity of sample into the flow-through cell to displace completely the wash water introduced during the wash cycle.

Those familiar with the art will understand that various modifications can be made without departing from the spirit of the present invention. For example, the embodiment disclosed above deals with a system for performing urinalysis. An adaptation of the invention to other forms of analysis may require different means for introducing the sample into the system, different solvents, etc. These and other changes may be made within the scope of the invention, which is defined solely by the claims appended hereto.

I claim:

1. Apparatus for microscopically analyzing fluids, comprising:
   sample container means for receiving and retaining a sample of fluid for analysis;
   video imaging means for electronically generating and displaying an image of a portion of said sample at a selected level of magnification, including video camera means for acquiring a visual image and generating electronic signals responsive to said at least one level of magnification, illuminating means for directing a beam of light through said sample toward said camera means, and monitor means operatively communicating with said camera for displaying said image;
   flow-through cell means, including
      display chamber means for disposing said portion of said sample in the path of said light beam;
      upper and lower retaining members, generally flat in form, the upper member having fluid flow passages formed therein;
      a central member, generally flat in form, having a peripheral area defining said display chamber, said chamber being in registration with said fluid flow passages;
      said members being secured to one another to form an integral, laminated structure; and
      a body, having a flat central well carrying said laminated structure, and having a viewing aperture formed therein, said aperture underlying at least a portion of said display chamber;
   a wash fluid reservoir for retaining a supply of wash fluid; and
   pump means in fluid communication with said flow-though cell means and in selective fluid communication with one of said sample container means or said wash fluid reservoir, for delivering to said flow-through cell means a quantity of said sample or said wash fluid.

2. The apparatus of claim 1, wherein said flow-through cell further includes connector pegs extending upward from said fluid flow passages.

3. The apparatus of claim 1, wherein said video imaging means has at least two levels of magnification.

4. The apparatus of claim 1, wherein said video imaging means displays said image in color.

* * * * *